United States Patent [19]

Krafft et al.

[11] Patent Number: 5,124,468
[45] Date of Patent: Jun. 23, 1992

[54] METHOD FOR SILYLFORMYLATING ALKYNES AND PRODUCTS OBTAINED THEREFROM

[75] Inventors: Terry E. Krafft, Longmont, Colo.; Jonathan D. Rich, Rexford; Timothy B. Burnell, Schenectady, both of N.Y.

[73] Assignee: General Electric Company, Schenectady, N.Y.

[21] Appl. No.: 739,360

[22] Filed: Aug. 2, 1991

[51] Int. Cl.$^5$ ................................. C07F 7/08
[52] U.S. Cl. ..................... 556/436; 556/464
[58] Field of Search ................ 556/436, 464

[56] References Cited

U.S. PATENT DOCUMENTS

| | | | |
|---|---|---|---|
| 2,588,083 | 3/1952 | Burkhard et al. | 556/436 |
| 3,256,308 | 6/1966 | Sterling et al. | 556/464 |
| 3,337,598 | 8/1967 | Sterling et al. | 556/464 |
| 4,383,122 | 5/1983 | Mukaiyama et al. | 556/436 X |
| 4,424,392 | 1/1984 | Petty | 556/436 |
| 4,675,426 | 6/1987 | Crivello | 556/464 |
| 4,914,220 | 4/1990 | Desmond et al. | 556/436 |

FOREIGN PATENT DOCUMENTS 0185791  9/1985  Japan ........................ 556/436

OTHER PUBLICATIONS

Matsuda et al., "J.A.C.S", 1989, 111, pp. 2332-2333.

*Primary Examiner*—Paul F. Shaver
*Attorney, Agent, or Firm*—William A. Teoli; James C. Davis, Jr.; William H. Pittman

[57] ABSTRACT

Silicon hydrides substituted with oxygen containing radicals such as alkoxy, can be silylformylated with alkynes and carbon monoxide in the presence of a rhodium catalyst to produce silyl alkenyl acetals. The silyl alkenyl acetals are useful as plasticizers for organosilicon copolymers.

22 Claims, No Drawings

METHOD FOR SILYLFORMYLATING ALKYNES AND PRODUCTS OBTAINED THEREFROM

BACKGROUND OF THE INVENTION

The present invention relates to a method for making silylalkenyl acetals. More particularly the present invention relates to a method for silylformylating alkynes with a silicon hydride, such as an alkoxy substituted silicon hydride and carbon monoxide in the presence of a rhodium catalyst.

A method for silylformylating alkynes is shown by Matsuda et al, JACS 1989, 111, 2332-2333. An alkyne is reacted with carbon monoxide and dimethylphenylsilane in the presence of a $Rh_4(CO)_{12}$ catalyst. A solution of the catalyst in benzene is used at a temperature of 100° C. and a pressure of 30 $Kg/cm^2$. Although the Matsuda et al method can be used to make various silylformylated alkenes, its scope is limited because it uses silicon hydride reactants which are substituted with non-functional radicals, i.e., hydrocarbon radicals attached to silicon by carbon-silicon bonds.

It is generally known that during the silylformylation of alkynes with a silicon hydride and carbon monoxide in the presence of a Group VIII metal catalyst, that a competing hydrosilylation reaction can occur. The silicon hydride, for example, can react with the silylalkenyl hydroformylated reaction product normally formed during the silylformylation reaction. In instances where functional silanes are used, such as halosilanes, hydrosilylation can be a significant side reaction which can drastically reduce the yield of the desired silylalkenyl reaction product.

It would be desirable therefore to provide a method for silylformylating alkynes utilizing silanes having functional groups in place of inert hydrocarbon radicals attached to silicon by carbon silicon bonds. Such novel silylformylated reaction products of alkynes would provide silanes having reactive functional groups which would enhance the utility of such materials as intermediates in chemical synthesis.

SUMMARY OF THE INVENTION

The present invention is based on the discovery that silicon hydrides having the formula, $$(R)_n(R^1)_{3-n}SiH, \quad (1)$$

can be reacted with an alkyne having the formula, $$R^2C\equiv CR^3, \quad (2)$$

in the presence of carbon monoxide and a rhodium catalyst at a temperature in the range of from $-20°$ C. to 200° C., to produce a variety of organofunctional silanes, where R is a monovalent radical attached to silicon by a silicon-oxygen linkage, such as $C_{(1-8)}$ alkoxy, $C_{(6-12)}$ aryloxy, and triorganosiloxy, $R^1$ is a $C_{(1-13)}$ monovalent hydrocarbon radical, $R^2$ and $R^3$ are the same or different monovalent radicals selected from the class consisting of hydrogen and a $C_{(1-3)}$ organic radical, and n is an integer equal to 1 to 3 inclusive.

There are included among the organofunctional silanes, geometric isomeric $\alpha,\beta$-unsaturated silyl aldehydes, which can be in cis or trans form, and silylalkenyl acetals having the formula,

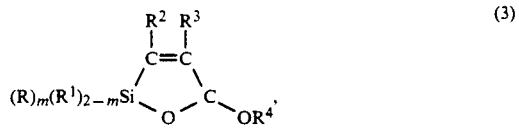

where R, $R^1$, $R^2$ and $R^3$ are as previously defined, $R^4$ is a member selected from $R^1$ and $Si(R^1)_3$ and m is a whole number equal to 0 to 2 inclusive. The following equation further shows the formation of the geometric isomeric aldehydes which can be in cis or trans form, and the silyl alkenyl acetal formed in the silylformylation reaction:

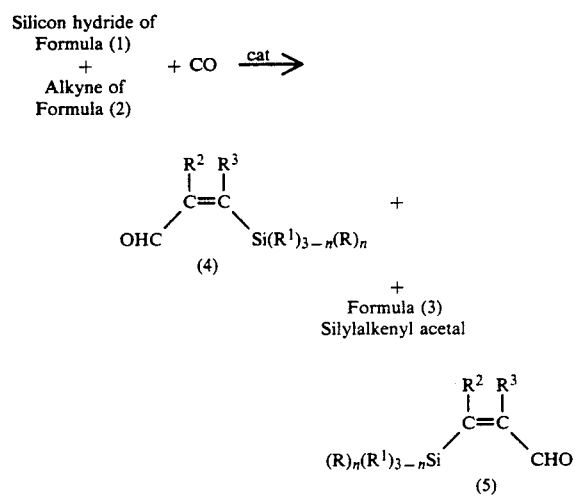

Radicals included within R of formulas (4) and (5) are for example, $C_{(1-8)}$ alkoxy, such as, methoxy, ethoxy, propoxy, $C_{(6-13)}$ aryloxy such as, phenoxy, cresoxy and napthoxy; triorganosiloxy such as, trimethylsiloxy, dimethylphenylsiloxy. Radicals included by $R^1$ are for example, $C_{(1-8)}$ alkyl such as, methyl, ethyl, propyl, butyl, and $C_{(6-13)}$ aryl such as, phenyl, tolyl, xylyl, and napthyl. Radicals included within $R^2$ and $R^3$ are organic radicals which can contain chemically combined N, O, S, and halogen atoms and mixtures thereof, in addition to carbon and hydrogen. Some of the $R^2$ and $R^3$ radicals are monovalent hydrocarbon radicals defined by $R^1$, and hydroxy methyl, carbomethoxy, carboethoxy, chloromethyl, chloropropyl, aminoethyl and aminopropyl.

STATEMENT OF THE INVENTION

There is provided by the present invention, a method comprising, (1) effecting reaction between a silicon hydride of formula (1), and an alkyne of formula (2) in the presence of carbon monoxide and an effective amount of a rhodium catalyst and, (2) recovering silylformylated alkyne reaction product from the mixture of (1).

Some of the silylalkenyl acetals included within formula (3) are,

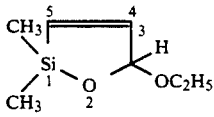

1,1(dimethyl)-2-oxa-3-ethoxysilacyclopent-4,5-ene,
1,1(dimethyl)-2-oxa-3-methoxysilacyclopent-4,5-ene,
cis and trans; 1-ethoxy-1-methyl-1-2-oxa-3-ethoxy silacyclopent-4,5-ene,
cis and trans; 1-methoxy-1-methyl-1-2-oxa-3-methoxy silacyclopent-4,5-ene,
1,1-diethoxy-2-oxa-3-ethoxysilacyclopent-4,5-ene,
1,1-dimethoxy-2-oxa-3-ethoxysilaclopent-4,5-ene,
1,1-dimethyl-2-oxa-3-ethoxy-4-phenylsilacyclopent-4,5-ene,
cis and trans; 1-ethoxy-1-methyl-2-oxa-3-ethoxy-4-phenylsilacyclopent-4,5-ene,
1,1-diethoxy-2-oxa-3-ethoxy-4-phenylsilacyclopent-4,5-ene,
1,1-dimethyl-1-2-oxa-3-ethoxy-4,5-diphenyl silacyclopent-4,5-ene,
cis and trans; 1-ethoxy-1-methyl-2-oxa-3-ethoxy-4,5-diphenylsilacyclopent-4,5-ene,
1,1-diethoxy-2-oxa-3-ethoxy-4,5-diphenyl silacyclopent-4,5-ene,
1,1-dimethyl-2-oxa-3-ethoxy-4,5-dicarbomethoxy silacyclopent-4,5-ene,
cis and trans; 1-ethoxy-1-methyl-2-oxa-3-ethoxy-4,5-dicarbomethoxysilacyclopent-4,5-ene,
1,1-diethoxy-2-oxa-3-ethoxy-4,5-dicarbomethoxy silacyclopent-4,5-ene,
1,1-dimethyl-2-oxa-3-ethoxy-4,5-di(hydroxymethyl)-silacyclopent-4,5-ene,
cis and trans; 1-ethoxy-1-methyl-2-oxa-3-ethoxy-4,5-di(-hydroxymethyl)silacyclopent-4,5-ene,
1,1-diethoxy-2-oxa-3-ethoxy-4,5-di(hydroxymethyl)-silacyclopent-4,5-ene, In addition to silylalkenyl acetals of formula (3), additional reaction products which can be made in accordance with the practice of the invention are aldehydes such as,

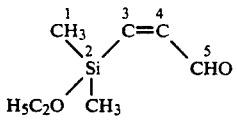

E and Z; 2-ethoxy-2-methyl-2-silapent-3-enal
E and Z; 2,2-diethoxy-2-silapent-3-enal
E and Z; 1,1,1-triethoxysilabut-2-enal
E and Z; 2-ethoxy-2-methyl-4-phenylsilapent-3-enal
E and Z; 2,2-diethoxy-4-phenylsilapent-3-nal
E and Z; 1,1,1-triethoxy-3-phenylsilabut-2-enal
E and Z; 2-ethoxy-2-methyl-3,4-diphenylsilapent-3-enal
E and Z; 2,2-diethoxy-3,4-diphenylsilapent-3-enal
E and Z; 1,1,1-triethoxy-2,3-diphenylsilabut-2-enal
E and Z; 2-ethoxy-2-methyl-3,4-di(carbomethoxy)silapent-3-enal
E and Z; 2,2-diethoxy-3,4-di(carboethoxy)silapent-3-enal
E and Z; 1,1,1-triethoxy-2,3-di(carbomethoxy)silapent-3-enal
E and Z; 2-ethoxy, 2-methyl-3,4-di(hydroxymethyl)silapent-3-enal
E and Z; 2,2-diethoxy-3,4-di(hydroxymethyl)silapent-3-enal
E and Z; 1,1,1-triethoxy-2,3-di(hydroxymethyl)silabut-2-enal There is included within rhodium catalyst which can be employed in the practice of the present invention compounds such as, dodecacarbonyl tetrarhodium, dodecacarbonyl dicobalt dirhodium, rhodium trichloride. An effective amount of rhodium catalyst is 0.01% to 5% by weight rhodium based on the weight of the silylformylation reaction mixture.

In the practice of the preferred form of the present invention, carbon monoxide can be introduced into a sealed reactor containing the rhodium catalyst, the silane, and the alkyne in further combination with an organic solvent and cocatalyst, such as a tertiary amine. Suitable organic solvents are for example, toluene, benzene, mesitylene, hexane, heptane, dodecane, and chlorobenzene. Suitable tertiary amines are for example, trimethylamine, triethylamine, tributylamine, pyridine, and piperidine. It is preferred to conduct the reaction under substantially anhydrous conditions such as using a nitrogen atmosphere.

Although ambient conditions are preferably used, temperatures in the range of from $-20$ C. to $200°$ C. and pressures set from 300 psi to 3000 psi, can be employed in particular situations. Recovery of the product can be achieved by standard techniques, such as filtering the mixture of solids, distilling the mixture of volatiles, and thereafter recovering reaction product under reduced pressure.

The silylalkenyl acetals of the present invention can be used as plasticizers for organo thermoplastic polymers such as, polypropylene, polyesters, and polycarbonates. In addition these cyclic acetals also can be used as adhesion promotors, glass sizing agents, coupling compounds, and waterproofing additives. The aldehydes can be used as intermediates for synthesizing silanes and as plasticizers for thermoplastic polymers.

The following examples are given by way of illustration and not by way of limitation. All parts are by weight unless otherwise indicated.

EXAMPLE 1

Carbon monoxide was introduced into a reactor at a pressure of 495 psi. The reactor contained a mixture under a nitrogen atmosphere which was stirred at room temperature consisting of 0.15 g (0.20 mmol) of $Rh_4(CO)_{12}$, 2.06 g (0.020 mol) of dimethylethoxysilane, 2.25 g (0.022 mol) of phenylacetylene, 2.79 mL (0.020 mol) of triethylamine and 50 mL of dry toluene. After 18 hours of stirring, a GC analysis showed that the reaction was complete. There was obtained a yield of 1,1-dimethyl-2-oxa-3-ethoxy-4-phenyl silacyclopent-4,5-ene, and 69% by weight of a mixture of E and Z; 2-ethoxy-2-methyl-4-phenylsilapent-3-enal. The products were isolated by vacuum distillation and analyzed by $^1$H NMR. (EtO)Me$_2$SiCH=CPhCHO(Z isomer) $^1$H NMR(CDCl$_3$)10.19(s,CHO),7.2-7.5(Ph), 6.96($H_{olefin}$), 3.75 (q,—CH$_2$—, J=7.0), 1.23 (t,CH$_3$—C,J=7.0), 0.39 (s,CH$_3$—Si). (EtO)Me$_2$Si—CH=CPhCHO (E isomer) $^1$H NMR(CDCl$_3$)9.68 (s,CHO), 7.1-7.6 (Ph), 6.89 (S,$H_{olefin}$), 3.58 (q,—CH$_2$—,J=7.0), 1.13 (t,CH$_3$—C,J=7.0), 0.02 (s,CH$_3$—Si). Me$_2$SiCH=CPhCH(OEt)O $^1$H NMR (CDCl$_3$) 6.57 (s,H$_{olefin}$), 6.05 (s,H—COSi), 3.78(dq,—CHH$_a$—, $^2J_{H—H}$=9.3, $^3J_{H—Me}$=7.1), 3.68 (dq, —CHH$_b$—,$^2J_{H—H}$=9.3, $^3J_{H—}$ Me=7.1), 1.21 (t, CH₃—C, J=7.1), 0.38 (s, Me$_a$—Si), 0.31 (s, Me$_b$—Si).

EXAMPLE 2

In accordance with the procedure of Example 1, carbon monoxide was introduced into a reactor at a pressure of 520 psi. The reactor contained a mixture which was stirred at room temperature consisting of 0.149 g (0.20 mmol) of Rh$_4$(CO)$_{12}$, 3.23 g (0.020 mol) of triethoxysilane, 2.25 g (0.022 mol) of phenylacetylene, 2.79 mL (0.020 mol). After 10 minutes, the GC analysis showed that only 50% of the reagents had reacted. After stirring an addition 30 minutes the reaction was complete and GC analysis indicated a 93% yield of product. Based on method of preparation and IR, there was obtained about a 37% yield of 1,1-diethoxy-2-oxa-3-ethoxy-4-phenylsilacyclopent-4,5-ene, and 56% yield of an isomeric mixture of E and Z; 1,1,1-triethoxy-3-phenylsilabut-2-enal.

EXAMPLE 3

In accordance with the procedure of Example 1, carbon monoxide was introduced into a reaction mixture at 520 psi which was stirred at room temperature under a nitrogen atmosphere and consisted of 0.04 g (0.20 mmol) of rhodium trichloride, 2.06 g (0.020 mol) of dimethylethoxysilane, 2.25 g (0.022 mol) of phenylacetylene, 2.79 mL (0.020 mol) of triethylamine and 50 mL of dry toluene under a nitrogen atmosphere. After 35 minutes, GC analysis showed that no reaction had taken place. The mixture was then stirred at 90° C. for 1 hour and GC analysis showed that the reaction was complete. There was obtained a 3% yield of acetal and a 76% yield of aldehyde product.

EXAMPLE 4

Carbon monoxide was charged at a pressure of 400 psi into a reactor containing a mixture of 0.15 g (0.20 mmol) of Rh$_4$(CO)$_{12}$, 2.06 g (0.020 mol) of dimethylethoxysilane, 2.79 mL (0.020 mol) of triethylamine and 50 mL of dry toluene under a nitrogen atmosphere. The mixture had been cooled to a −94° C. and 1.2 g (46 mmol) of acetylene was allowed to condense into the reactor. The mixture was slowly warmed to room temperature after the carbon monoxide had been introduced. The reaction was complete after 1½ hours and GC indicated that a 60% yield of product was obtained. Based on method of preparation and IR there was obtained a 35% yield of E and Z; 2-ethoxy-2-methylsilapent-3-enal.

Although the above examples are directed to only a few of the very many variables which can be used in the practice of the present invention, it should be understood that the present invention is directed to a method and products obtained therefrom which are set forth in the description preceding these examples.

What is claimed is:

1. A method comprising,
   (1) effecting reaction between an alkyne of the formula,

R²C≡CR³ and a silicon hydride of the formula,

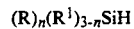

(R)$_n$(R¹)$_{3-n}$SiH in the presence of carbon monoxide and an effective amount of a rhodium catalyst and,
   (2) recovering a silylformylated alkyne reaction product from the mixture of (1), where R is a monovalent radical attached to silicon by a silicon oxygen linkage, R¹ is a C$_{(1-13)}$ monovalent hydrocarbon radical, R² and R³ are the same or different monovalent radicals selected from the class consisting of hydrogen and a C$_{(1-3)}$ organic radical and n is an integer equal to 1 to 3 inclusive.

2. A method in accordance with claim 1, where the silicon hydride is an ethoxysilane.

3. A method in accordance with claim 1, where the alkyne is phenylacetylene.

4. A method in accordance with claim 1, where the alkyne is acetylene.

5. A method in accordance with claim 1, where the alkyne is diphenylacetylene.

6. A method in accordance with claim 1, where the alkyne is but-2-yne-1,4-diol.

7. A method in accordance with claim 1, where the alkyne is dimethylacetylene dicarboxylate.

8. A method in accordance with claim 1, where the rhodium catalyst is Rh$_4$(CO)$_{12}$.

9. A method in accordance with claim 1, where the rhodium catalyst is rhodium trichloride.

10. Silyl alkenyl acetals having the formula,

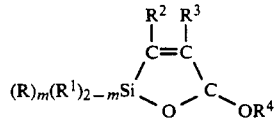

where R is a monovalent radical attached to silicon by silicon oxygen linkage, R¹ is a C$_{(1-13)}$ monovalent hydrocarbon radical, R² and R³ are the same or different monovalent radicals and selected from the class consisting of hydrogen and a C$_{(1-13)}$ organic radical, R⁴ is a monovalent radical selected from the class consisting of C$_{(1-8)}$ alkyl, C$_{(6-13)}$ aryl and C$_{(1-3)}$ triorganosilyl, and m is a whole number equal to 0 to 2.

11. Silylalkenyl aldehydes having the formula,

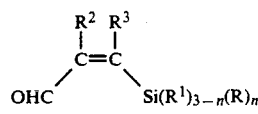

where R is a monovalent radical attached to silicon by a silicon-oxygen linkage, such as C$_{(1-8)}$ alkoxy, C$_{(6-2)}$ aryloxy, and triorganosiloxy, R¹ is a C$_{(1-13)}$ monovalent hydrocarbon radical, R² and R³ are the same or different monovalent radicals selected from the class consisting of hydrogen and a C$_{(1-13)}$ organic radical, and n is an integer equal to 1 to 3 inclusive.

12. Silylalkenyl aldehydes having the formula,

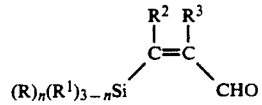

where R is a monovalent radical attached to silicon by a silicon-oxygen linkage, such as C$_{(1-8)}$ alkoxy, C$_{(6-12)}$ aryloxy, and triorganosiloxy, R¹ is a C$_{(1-13)}$ monovalent hydrocarbon radical, R² and R³ are the same or different monovalent radicals selected from the class consisting of hydrogen and a $C_{(1-3)}$ organic radical, and n is an integer equal to 1 to 3 inclusive.

13. E; 2-ethoxy-2-methyl-4-phenylsilapent-3-enal in accordance with claim 11.

14. Z; 2-ethoxy-2-methyl-4-phenylsilapent-3-enal in accordance with claim 11.

15. E; 1,1,1-triethoxy-3-phenylsilabut-2-enal in accordance with claim 11.

16. Z; 1,1,1-triethoxy-3-phenylsilabut-2-enal in accordance with claim 11.

17. 1,1-dimethyl-2-oxa-3-ethoxy-4-phenyl silacyclopent-4,5-ene, in accordance with claim 10.

18. 1,1-diethoxy-2-oxa-3-ethoxy-4-phenyl silacyclopent-4,5-ene, in accordance with claim 10.

19. E; 2-ethoxy-2-methyl-3-phenylsilapent-3-enal in accordance with claim 12.

20. Z; 2-ethoxy-2-methyl-3-phenylsilapent-3-enal in accordance with claim 12.

21. E; 1,1,1-triethoxy-2-phenylsilabut-2-enal in accordance with claim 12.

22. Z; 1,1,1-triethoxy-2-phenylsilabut-2-enal in accordance with claim 12.

* * * * *